United States Patent [19]

McKay et al.

[11] Patent Number: 5,270,191
[45] Date of Patent: Dec. 14, 1993

[54] METHOD FOR MANIPULATION OF THE CELL TYPES OF EUKARYOTES

[75] Inventors: Ronald D. G. McKay, Brookline, Mass.; Parmjit S. Jat, Islington, England; Guillermina Almazan, Cambridge, Mass.

[73] Assignee: Massachusetts Institute of Technology, Cambridge, Mass.

[21] Appl. No.: 883,886

[22] Filed: May 12, 1992

Related U.S. Application Data

[63] Continuation of Ser. No. 201,762, Jun. 2, 1988, abandoned, which is a continuation-in-part of Ser. No. 180,548, Apr. 12, 1988, abandoned.

[51] Int. Cl.$^5$ .................. C12N 15/00; C12N 5/00
[52] U.S. Cl. .................. 435/172.3; 435/240.2; 935/70
[58] Field of Search .............. 435/172.3, 240.2, 235; 935/32, 57, 70

[56] References Cited

U.S. PATENT DOCUMENTS 4,707,448 11/1987 Major ...................... 435/240.25

FOREIGN PATENT DOCUMENTS

WO89/03872 10/1987 PCT Int'l Appl.

OTHER PUBLICATIONS

Jat, P. S. and P. A. Sharp, *J. Virol.*, 59:746–750 (1986).
Chou, J. Y., *Methods in Enzymology*, 109:385–395 (1985).
Jat, P. S., et al., *Molecular and Cellular Biology*, 6:1204–1217 (1986).
Hockfield, S. and R. D. G. McKay, *Journal of Neuroscience*, 5:3310–3328 (1985).
Frederiksen and R. D. G. McKay, *Journal of Neuroscience*, 8:1144–1151 (1988).
Jat, P. S. and P. A. Sharp, *Mol. Cell Biol.*, 9:1672–1681 (1989).
Frederiksen, K., et al., *Neuron*, 1:439–448 (Aug. 1988).
International Search Report.
Petit, C. A. et al., *Virology*, 127:74–82 (1983).
Beug, H. et al., *Cell*, 28:907–919 (1982).
Neto et al., *Devel. Brain Res.*, 26:11–22 (1986).
Pintel et al., *J. Virology*, 38:518–528 (1981).
Pancha et al., *J. Virology*, 57(1):50–64 (1986).
Jat et al., *Mol. Cell. Biol.*, 6:1204–1217 (1986).
Raff et al., *Nature*, 303:390–396 (1983).
Yasumoto, *Mol. Cell. Biol.*, 4:712–721 (1984).
Geller et al., *J. Cell Biol.*, 107:1977–1986 (1988).
Bartlett et al., *Proc. Natl. Acad. Sci.*, 85:3255–3259 (1988).
Harko et al., *Annals Neurology*, 20(5):573–582 (1986).
Neto et al., *Devel. Brain Res.*, 26:11–22 (1986).
Peden et al., *Experimental Cell Research*, 185:60–72 (1989).

*Primary Examiner*—Jasemine C. Chambers
*Attorney, Agent, or Firm*—Hamilton, Brook, Smith & Reynolds

[57] ABSTRACT

A novel method of immortalizing cell lines, as well as cell lines immortalized by the method. According to the method of the present invention, a gene which confers on a cell the ability to grow in tissue culture is introduced, using known techniques, into such a cell. This gene, referred to as a growth promoting gene, is under control such that when the gene action or function is turned down or off, the cell in which it resides switches to a new differentiated state. In one embodiment, the temperature sensitive (ts) form of the oncogene derived from the simian virus SV40 is the growth-promoting gene.

10 Claims, 2 Drawing Sheets

METHOD FOR MANIPULATION OF THE CELL TYPES OF EUKARYOTES

GOVERNMENT FUNDING

Work described herein was supported by funding from the National Institutes of Health) Contract No. NIH-2-ROI-NS21991-04).

RELATED APPLICATION

This is a continuation of co-pending application Ser. No. 07/201,762 filed on Jun. 2, 1988, now abandoned, which application Ser. No. 201,762 is a continuation-in-part of U.S. Serial No. 180,548, filed Apr. 12, 1988, now abandoned.

BACKGROUND

The multicellular eukaryotic organism is made up of many different cell types. Studies in modern biology have shown that specific genes are expressed in one cell type and not in another.

It is known that particular types of cell can be taken from an animal and grown in tissue culture for a short period. However, these primary cells have a limited life span in culture. Methods are available which allow cells to grow indefinitely in culture. For example, cells can be derived from tumors which have cell-type specific properties and grow continuously in culture. It is now known, however, that tumor cells differ from their normal counterparts because they have undergone heritable and specific changes at the DNA level which change the growth state of these cells. The genes which alter the growth state of cells when they are altered, either in their regulatory or effector properties, are known as oncogenes.

As a result, although tumor-derived cells have proven to be very useful, particularly because they make long-term growth of cells in culture possible, because they differ from corresponding normal cells in many ways, they have limited use in many applications. It would be useful to have a means of producing or growing quantities of normal cells with defined characteristics.

SUMMARY OF THE INVENTION

The present invention relates to a method of producing continuous cell lines, from vertebrates, which have defined characteristics and of deriving a differentiated cell from a continuous cell line, through the use of an oncogene whose function is controlled by an external factor, such as temperature, as well as to continuous cell lines which can differentiate, upon change in the external factor, such as temperature, which controls the oncogene function, and to recombinant retroviruses useful in the method of the present invention. According to the method of the present invention, a gene which confers on a cell of vertebrate origin the ability to grow in tissue culture is introduced, using known techniques, into such a cell. This gene, referred to as a growth promoting gene, is under control such that when the gene action or function is turned down or off, the cell in which it resides switches to a new, differentiated state. In one embodiment, the temperature sensitive (ts) form of the oncogene derived from the simian virus SV40 is introduced into a cell, which is subsequently maintained under conditions appropriate for its growth (i.e., for an increase in the number of such cells); these conditions include a temperature (in this case, 33° C.) at which the cells grow with the standard morphology of cell lines. Subsequently, the temperature is shifted (e.g., to 39° C.) to one at which the viral gene is inactivated. Through use of the method of the present invention, it is possible to obtain a proliferating cell line which can be grown rapidly in large numbers and, after the cell number has been expanded, to differentiate the cell into a preselected differentiated derivative. Thus, it provides a general method of generating precursor cell lines which are capable of further differentiation by introducing immortalizing oncogenes into eukaryotic cells and, thus, of obtaining differentiated derivatives from a continuous cell line.

BRIEF DESCRIPTION OF THE DRAWINGS

FIG. 2A-2B is a schematic representation of the construction of plasmid pZiptsa58U19.

DETAILED DESCRIPTION OF THE INVENTION

The present invention relates to a novel method of immortalizing cell lines, as well as to cell lines immortalized by the method and to recombinant retroviruses, which include a growth promoting gene, such as the temperature sensitive SV40 oncogene. In general, the method comprises introducing into cells of a selected type, in primary culture, a growth promoting gene, which enables the cells to grow, and whose function is controlled by an external factor. To make it possible to select cells which contain the growth promoting gene, a second gene encoding a selectable marker (e.g., drug resistance) is also introduced into the cells. Cells containing both the selectable marker and the growth promoting gene are selected (e.g., by plating onto media containing the drug against which the gene confers resistance) and isolated. The isolated cells are subsequently plated onto an appropriate medium, under conditions (e.g., temperature) under which the growth promoting gene is activated (e.g., permissive conditions). After allowing sufficient time for the cells to proliferate, the conditions (e.g., temperature) are switched to nonpermissive conditions (e.g., increased temperature) to inactivate the growth promoting gene, at which time the cells differentiate.

In a particular embodiment of the present invention, the temperature sensitive oncogene derived from the simian virus SV40 is the growth promoting gene. The temperature sensitive domain of the tsA58 strain of the SV40 virus was recombined with the wild type (not temperature sensitive) form of the SV40 antigen, which was present in a recombinant retrovirus (described in detail in Example 1). Tegtmeyer, P. et al., Journal of Virology, 16:168-178 (1975). This made it possible to introduce the temperature sensitive oncogene with high efficiency into primary cells.

Primary cells used in the work described below and in the Examples were cells from the nervous system. However, it is to be understood that the method of the present invention can be used to immortalize any type of eukaryotic cell of interest. In addition, although the description of the method of the present invention presented below makes specific reference to the use of a retroviral vector for introduction of a growth promoting gene which is an oncogene, it is to be understood that other known methods (e.g., electroporation, microinjection) can also be used for this purpose. It is also possible to introduce conditionally immortalized cells into animals (e.g., mice, rats, rabbits) to produce transgenic animals in which the growth promoting gene is inactive at normal body temperatures. Because they are present in such animals at the nonpermissive temperature, the ts or otherwise conditionally immortalized cells should be able to differentiate in vivo. The oncogene described below is the temperature sensitive domain of the tsA58 strain of SV40 virus. However, other oncogenes can also be used in the present method.

The method of the present invention has been carried out in cells from the nervous system. Because the cell types present in the developing brain had previously been characterized, it was possible to verify that differentiated cells produced by the method do, in fact, have the characteristics of neurons or glia. This provides direct verification of the ability of the present method to produce a continuous cell line from which pre-selected differentiated derivatives can be produced through control of the growth promoting gene.

Two regions of the embryonic rat nervous system were chosen as a source of primary cells: the hippocampus and the cerebellum. Primary cells were plated in tissue culture and exposed to a synthetic retrovirus (see Example 1) carrying the temperature sensitive form of SV40 T antigen. The retrovirus also contains a gene encoding drug resistance (i.e., G418 resistance), which served as the basis for selecting cells containing the retrovirus. Immortal cell lines expressing SV40 T antigen were obtained from these cultures by growing the cells at 33° C. in drug-containing medium. Those cells containing the G418 resistance gene (Neo) grew in the drug-containing medium; those lacking the gene did not survive. At 33° C., the surviving cells grew with the standard morphology of cell lines. Clonal cells were obtained by picking colonies using cloning rings. The test of the concept is the response of the cells when they are grown at 39° C. The criteria chosen for cellular response were morphology, immunohistochemistry and immunochemistry. The method used and the data obtained are described in detail in the Examples and demonstrate that when the temperature is raised, cells can differentiate to a differentiated state characteristic of neurons and glia. The methods used in verifying that the resulting differentiated cells have such characteristics are also described in the Examples.

A continuous cell line which is a precursor cell line which differentiates into mature oligodendrocytes has also been produced, using an approach similar to that described above. Oligodendrocytes, the myelin-forming cells of the CNS, develop during the first week of postnatal life in the optic nerve of the rat. Their progenitors are bipotential cells which also give rise to type 2 astroctyes. To obtain permanent cell lines, primary cultures from the optic nerve of 3-day-old Sprague Dawley (SD) rats were infected with a retrovirus vector transducing the tsA58/U19 combination large SV40 T oncogene. At the permissive temperature, one of the derived cell lines proliferates and expresses the T antigen and small amounts of GC (galactocerebroside), a surface lipid marker for oligodendrocytes and $A_2B_5$ (surface gangliosides). At the non-permissive temperature, the cells lose the T antigen expression, stop proliferating, and stain very strongly with GC and $A_2B_5$ antibodies. The two main protein components of myelin, MBP (myelin basic protein) and PLP (proteolipid protein) are also expressed. $A_2B_5$ and GC are selectable markers which are highly specific for either precursor or mature oligodendrocytes (e.g., GC is a lipid present only on oligodendrocytes). MB and PLP are two myelinating oligodendrocyte markers. Use of these selectable markers resulted in highly specific selection of an oligodendrocyte precursor which can differentiate into mature oligodendrocytes when the immortalizing gene was inactivated (in this case, by shifting the temperature at which the cells were being maintained to a nonpermissive temperature of 39° C.). Construction of such a cell line is described in Example 3. An oligodendrocyte optic nerve cell line (ts U195) has been deposited (Jun. 1, 1988) at the American Type Culture Collection (Rockville, Md.), under the terms of the Budapest Treaty, and has been assigned ATCC accession number CRL 9729.

These results show that a precursor cell line spontaneously differentiates into a mature oligodendrocyte when the immortalizing oncogene is inactivated. The functionality or potential use as replacement therapy of these cells will further be explored in transplantation experiments using myelin deficient mutant rodents. For example, in rodents (e.g., mice, rats) there are dysmyelinating mutants, such as those described by Jaque and co-workers. Jaque, C. et al , *Journal of Neurochemistry*, 41:1335-1340 (1983). Oligodendrocytes produced according to the present method can be assessed for their effectiveness in reversing (partially or completely) the effects of such a genetic defect, which normally results in debilitation and death in animals in which the defect occurs. For example, murine mutants such as those described by Jaque and co-workers, which have defective myelination in the central nervous system and/or the peripheral nervous system, can be used to investigate the effectiveness of such cells. Correction of the defect will be evidenced by survival of the animals or less severe effects of the dysmyelination.

Cell lines of the present invention, in which oncogene expression is regulated, differ from currently available cell lines, in which the agent which establishes the cell line is not normally under external control. As a result, it is possible with this new technique to obtain proliferating cell lines which can be grown rapidly in large numbers and then to cause this cell to become a differentiated derivative. Until development of the present method, it was difficult or impossible to obtain such derivatives (e.g., because they grow much less rapidly and/or do not grow at all).

The method of the present invention provides a means by which large numbers of differentiated cells can be produced. Cells conditionally immortalized by the method of the present invention have diagnostic and therapeutic applications. For example, if a large quantity of a specific type of differentiated cell is needed for use in diagnostic methods, for transplantation into an individual or for use as a means of producing a desired product (e.g., protein, hormone, etc.), appropriate precursor (nondifferentiated) cells can be selected, using known techniques. They can subsequently be modified by introduction of a growth promoting gene, such as an oncogene, and cultured under permissive conditions (i.e., conditions under which the growth promoting gene is activated). When differentiated cells are needed, the cells are switched to conditions under which the growth promoting gene is inactivated. As a result, the previously undifferentiated cells are altered, producing the desired differentiated cells.

Alternatively, conditionally immortalized cells can be introduced (at a permissive temperature) into an individual, in whom they will reside at the nonpermissive (i.e., body) temperature. As a result, they will differentiate, thus providing an "internal" source of the desired type of differentiated cell.

Recent work on CNS transplants has been exciting and suggests rational approaches to therapy for CNS injury. Sladek, J.R. and D.M. Gash, *Neural Transplants: Development and Function*, Plenum Press, N.Y. (1984). The work described herein is directly relevant to transplant studies. Methods developed to identify and count cells will be useful in analyzing the fate of transplanted cells or the behavior of cells after injury. The present method of generating immortal cell lines which differentiate in vivo should be very important for cell replacement therapies.

The human demyelinating disease progressive multifocal leucoencapalopathy, PML, is associated with the JC virus infection (ZuRhein, G.M., *Prog. Med. Virol.*, 11:185-206 (1969); Padgett et al., *Lancet*, i:1257-1259 (1971); Padgett, B.L. and D.L. Walker, *Prog. Med. Virol.*, 22:1-34 (1976). In recent work, transgenic mice have been developed which express the early gene of the JC papovavirus associated with PML. These animals fail to myelinate their CNS (Small et al., 1986). This is an important finding because it shows that the whole course of viral infection is not necessary to cause disease—the early gene alone is sufficient. The action of the early gene (T antigen) to disrupt oligodendrocyte differentiation may occur either by the action of T antigen directly in oligodendrocyte precursors or indirectly in another cell type which regulates oligodendrocyte differentiation. Type 1 astrocytes are candidates for the site of action of T antigen function in causing PML as they are known to play an important role in the differentiation of oligodendrocyte precursors. Noble, M. and K. Murray, *EMBO Journal*, 3:2243-2247 (1984); Raff et al., *Cell*, 42:61-69 (1985). Retroviral vectors expressing papovavirus T antigens have been constructed and shown capable of immortalizing astrocytic precursors. Such immortalized precursors can be used to produce large numbers of differentiated cells and, thus, in the production of oligodendrocytes.

While multiple sclerosis is not clearly associated with a virus, the differentiation of oligodendrocytes is disturbed (McKhann, G.M., *Ann. Rev. Neurosci.*, 5:219-239 (1982). The use of synthetic retroviruses carrying papovavirus T antigens to infect the cells of the early nervous system provides an unusual opportunity to manipulate the cell types which interact to control oligodendrocyte differentiation.

Many neural tumors are histologically related to cells found in the early nervous system (Rubinstein, L.J , *J. Neurosurg.*, 62:795-805 (1985). From the viewpoint of both fundamental knowledge of the signalling systems in the embryonic nervous system and the management of neural disease, it is crucial to characterize the factors controlling the differentiation of neural cells and to determine how oncogenes disrupt differentiation. This can be accomplished using the method and conditionally immortalized cells of the present invention.

The present invention will now be illustrated by the following Examples, which are not to be seen as limiting in any way.

EXAMPLE 1

Construction of Retroviruses Carrying Oncogenes and a Dominant Selectable Marker pZipSV40tsA58

The recombinant retrovirus pZipSV40tsA58 was constructed by the insertion of the BglI-HpaI fragment of the SV40 tsA58 early region into the BamHI site of the pZipNeoSV shuttle vector in the sense orientation with respect to viral transcription. Cepko, C. et al., *Cell*, 37:1053-1062 (1984); Jat, P.S. et al., *Molecular and Cellular Biology*, 6:1204-1217 (1986); Jat, P.S. and P.A. Sharp, *Journal of Virology*, 59:746-750 (1986), the teachings of which are incorporated herein by reference. This SV40 fragment lacks both promoter and polyadenylation sites. Consequently, transcription of T antigen sequences is exclusively initiated in the viral LTR. The recombinant plasmid was transfected into the psi 2 helper cell line and neomycin resistant cell lines were derived by G418 selection. Mann, R. et al., *Cell*, 33:153-159 (1983), the teachings of which are incorporated herein by reference. These cell lines secrete defective helper free recombinant retroviruses carrying the thermolabile T antigen gene. The titre of recombinant virus was established by infection of 3T3 cells. By growing these 3T3 cell lines at 33° and 39° C., it was determined by immunohistochemistry and immunoprecipitation that they synthesize a ts form of SV40 T antigen. Culture medium from one of the highest titre psi 2 lines, psi2SVtsA58-4 ($10^4$ neo.resistant 3T3 units/ml.), was the source of virus for the infection of primary cultures of rat neural cells.

The target cells for viral infection were derived from the E18 entorhinal cortex and the P 2 cerebellum. The cells were dissociated by incubation in PBS, 0.5 mm EDTA, 0.25% trypsin, at 37° C. for 20-30 minutes. The trypsin solution was removed and replaced with DMEM, 10% fetal bovine serum. The cells were triturated by 10-20 passages through a narrow bor pasteur pipette. The cell suspension was plated onto polyornithine coated tissue culture dishes at a density of $10^5$ cells/cm². Cell survival was greater than 70%, as determined by fluorescein diacetate uptake. Several schedules were examined for the optimal time of infection from infection in suspension, 0 hrs., to 1 week post dissection. 4-12 hours after plating was found to yield the largest number of neo resistant colonies. Infection was achieved by replacing the culture medium on the attached cells with a small volume (0.8 ml./10 cm. dish) of sterile medium from the producer line psi2SVtsA58-4 containing 8 microgm./ml. of polybrene. The cells were incubated for 2 hours at 37° C. 8-10 volumes of 50—50 medium were then added and the cells plated at 33° C. The medium was changed the following day and four days postinfection, when selection for infected, neo resistant cells was initiated by the addition 0.2 mg./ml. G418 SO₄ (Geneticin, GIBCO). Cell death became apparent after 1 week of selection. Living colonies remained present in uninfected controls for as long as 1 month after the application of G418 selection. Resistant colonies were picked when they contained approximately 1000 cells. In general, primary embryonic brain cultures gave ten to thirty fold fewer colonies than a similar number of NIH 3T3 cells.

Cultures were passaged at high density and fed twice weekly. The 50/50 growth medium contained DMEM, 5% F.C.S., 2.5 microg./ml. insulin, 10 nm. progesterone, 10 pm. beta-estradiol, 1 microg./ml. transferrin, 0.1 mm. putrescine, 30 nm. sodium selenite, 0.3 nm. triiodothyronine, 20 nm. hydrocortisone, 2 mm. sodium pyruvate.

Other retroviruses can also be constructed, as described below.

Construction of pZipSV40 (U19) tsA58

Paucha et al. described a variant of SV40 T antigen (U19) which was deficient in certain viral functions, but has recently been shown to have enhanced ability to immortalize primary fibroblasts. Paucha, E. et al., *Journal of Virology*, 57:50-64 (1986); Jat, P.S. et al., *Molecular and Cellular Biology*, 6:1204-1217 (1986), the teachings of which are incorporated herein by reference. The U19 and tsA58 mutations fall in different parts of large T antigen. A retrovirus double mutant with both increased immortalization efficiency and thermolability has been constructed, as described in Example 3.

pZipPytsA (1T)

A retrovirus carrying the transforming early gene of polyoma virus can also be constructed and should be useful because cell culture suggests that the polyoma large T antigen has a less powerful effect on the immortalized cells than SV40 T antigen. Polyoma virus large T antigen immortalized primary fibroblasts are not transformed by supertransduction with the ras oncogene. In contrast, the ras oncogene will transform primary fibroblasts that have been immortalized with the SV40 T antigen. This result shows that polyoma and SV40 large T antigens interact with primary fibroblasts in different ways. One interpretation is that polyoma large T is 'milder' and this mild effect may be an advantage from the point of view of using the oncogenes for precursor cell immortalization. A temperature sensitive variant of mouse polyoma large T antigen is available. Fried, M., *Proceedings of the National Academy of Sciences, U.S.A*, 53:486-542 (1965).

Unlike SV40 early region, the early region of polyoma virus encodes two proteins with oncogenic properties. The middle T protein is transforming and the large T protein immortalizing. A useful retrovirus will contain only the sequences necessary for the large T antigen and the tsA form of this protein. A plasmid carrying the wild type large T cDNA and a second plasmid carrying the entire tsA early region have been constructed and generously provided by Dr. R. Kamen (Genetics Inst.). The region carrying the altered DNA sequences which confer thermolability can be placed into the large T cDNA and a retrovirus constructed.

pZipJCtsA

Evidence from transgenic mice shows that the human polyoma virus T antigen disrupts the differentiation of oligodendrocytes and may account for the demyelination found in the disease progressive multifocal leucoencapalopathy (PML). Papovavirus oncogenes, such as those derived from the three closely related viruses mouse polyoma, monkey SV40 and human JC can be used to construct a retrovirus. For example, the polyoma and SV40 thermolabile sequences can be placed onto the JC virus large T antigen.

EXAMPLE 2

Immortalization of Cerebellar Cells

Three different oncogenes, SV40 T antigen, v-myc and neu were tested for their ability to establish cell lines from the developing cerebellum. Materials and procedures used were as follows:

Markers Used to Identify Precursor Populations

Prior to establishing cell lines from the postnatal cerebellum, the proliferating cells which are potential targets for retroviral mediated gene transfer were identified. Three classes of antibody were used as markers to define the proliferative status of different cell types in the postnatal cerebellum: the monoclonal antibody Rat 401, anti-vimentin and anti-GFAP antibodies.

The monoclonal antibody Rat 401 recognizes a transient population of embryonic columnar epithelial cells and radial glial cells in many regions of the rat CNS. Hockfield, S. and R. McKay, *Journal of Neuroscience*, 12:3310-3328 (1985). The antibody recognizes a 200 Kd. protein and some smaller peptides which are variably found and may be degradation products. Known methods of measuring total cell numbers in the rat CNS during development were used with immunohistochemistry and techniques for labelling proliferating cells to show that Rat 401 recognized a major population of proliferating neuronal precursor cells in the spinal cord. Frederiksen, K. and R. McKay, *J. Neurosci.* (1987). In primary culture of embryonic brain cells a transient co-expression of the Rat 401 antigen and either neurofilaments or the astrocytic intermediate filament protein, GFAP, was seen in morphologically distinct cell types. This data suggests that the Rat 401 positive population contains precursors to both neurons and astrocytes. It has previously been shown in the cerebellum that the monoclonal antibody Rat 401 recognized a transient cell population. Hockfield, S. and R. McKay, *J. Neurosci.*, 5:3310-3328 (1985). These studies support the use of the Rat 401 antigen as an assay for precursor cell lines.

Vimentin is found in the precursor cells to the cerebellar granule neurons (Bovolenta, P. et al., *Dev. Biol.*, 102:248-259 (1984) as well as neuronal and glial precursor cells elsewhere in the nervous system. Vimentin is not generally found in mature neurons and astrocytes in vivo. About the time neurons become postmitotic, they begin to synthesize a specific set of intermediate filament proteins, neurofilaments, and lose vimentin expression.

Glial fibrilary acidic protein (GFAP) is the core intermediate filament protein which replaces vimentin in astrocytes (reviewed in Fields, 1985). This protein is expressed in the adult cerebellum in the radial Bergman glial cells and in astrocytes. GFAP is also found in some cells of the germinal zone of the monkey neuroepithelium during neurogenesis (Levitt, P. et al., *J. Neurosci.*, 1:27-39 (1981). These immunohistochemical observations and our quantitation of cell populations in vivo (Frederiksen, K. and R. McKay, *J. Neurosci.*, (1987)) suggested that there was a proliferating glial precursor cell which was Rat 401 negative and GFAP positive.

As Rat 401 antigen, vimentin and GFAP are potential markers for distinct precursor populations, the differential expression of these antigens was used to characterize cell populations in the postnatal cerebellum. Dissociated cerebellar cells were stained with Rat 401, anti-vimentin and anti-GFAP antibodies. The proportion of Rat 401 positive cells declines to zero before postnatal day 15 (P15), showing that Rat 401 is a precursor cell marker and confirming previous immunohistochemical analysis of cell differentiation in the postnatal cerebellum. The proportion of vimentin positive cells is much larger than the proportion of Rat 401 positive cells but also declines over this period. The proportion of GFAP positive cells is initially lower than the proportion of Rat 401 positive cells but by the end of the second postnatal week the number of GFAP positive cells increases while the expression of Rat 401 is lost.

These three markers are differentially expressed in cerebellar cell populations but further data is needed to establish if these cell populations are independent of one another and actively proliferating. The overlap in cell populations was determined by double label immunohistochemistry (Table 1) and the proliferative status of the antigenically distinct cell types was measured by an in vivo pulse of tritiated thymidine followed by immunohistochemistry and autoradiography on dissociated cells (Table 2).

Double immunohistochemistry showed that the Rat 401 positive population was a subset of the vimentin population but the autoradiographic data shows that these two populations are not in identical proliferative states. The GFAP positive population and the vimentin positive populations also overlap.

Animals, Cell Lines and Antibodies

Sprague Dawley rats were obtained from Taconic Inc., N.Y. NIH 3T3 cells and psi2 cells lines were grown in Dulbecco's modified Eagle's medium (DMEM) with 10% (v/v) calf serum, penicillin and streptomycin. The anti-vimentin antibody was obtained from ICN (Cat. No. 69-127), the anti-GFAP antibody was obtained from ICN (Cat. No. 69-110), and the anti-neurofilament antibody was Sternberger-Meyer (Cat. No. SMI 31), the Rat 401 antibody was established in this group and has been previously described (Hockfield, S. and R. McKay, *J. Neurosci.*, 5:3310-3328 (1985)), the anti-T antibody was monoclonal antibody 412 prepared by E. Harlow, the anti-Gal C antibody has been previously described Ranscht et al., 1982. In double label experiments rabbit anti-vimentin was obtained from R. Hynes, the rabbit anti GFAP from L. Eng., the rabbit anti-neurofilament was purchased from ICN (Cat. No. 20074). Secondary antibodies were obtained from Cappel-Worthington.

Analysis of Cerebellar Cells Types In Vivo

A detailed description of dissociation protocols, autoradiographic procedures and control experiments for cell numbers and staining procedures can be found in Frederiksen, K. and R. McKay, *J. Neurosci.* (1987). The cerebellum was dissected from postnatal rats and the cells dissociated by trituration after digestion in 0.15% trypsin in Ca++ and Mg++ free phosphate buffered saline. Measured aliquots of the dissociated cell suspension were spun onto coverslips and stained with primary antibodies and either fluorescein, rhodamine or peroxidase conjugated second antibodies. The data shown was derived from four or more animals from two or more litters.

Primary Cultures and Infection Protocols

The cerebellum was removed from P2 animals and incubated in 0.08% trypsin for 30 minutes at 37° C. After further dissection into small pieces the cells were dissociated by trituration in DMEM, 10% fetal calf serum using a 20 microlitre pipetteman. The cell suspension was plated onto polyornithine coated tissue culture dishes (15 micrograms/ml, Sigma) in DMEM, 10% fetal calf serum and incubated at 37° C. 24 hours after plating the cells were infected for 2 hours with the recombinant retroviruses in 8 micrograms/ml (Aldrich). After infection the virus containing medium was replaced with fresh DMEM, 10% fetal calf serum. tsA58 infected cell lines were subsequently grown at 33° C. 48 hours after infection the cultures were passaged and subjected to selection in 0.2 micrograms/ml G418 (Geneticin, Gibco). The medium was changed with fresh G418 every 3-4 days. Within three weeks control uninfected dishes had very few remaining cells and the infected dishes had macroscopic G418 resistant colonies. Colonies were picked using cloning rings and expanded into 96 well plates.

Growth and Characterization of Cell Lines

The cells were continually grown in DMEM and 10% fetal calf serum. The neu infected cells could be expanded and frozen but always grew slowly. The v-myc and T-antigen derived cells grew rapidly for a year and were subcloned. The immunohistochemical analysis of antigen expression in St15A cells was carried out in DMEM and selected batches of fetal calf serum at 33° C. and 39° C. The immunoblotting procedure was as described by Twobin et al. (1979). Analysis of proviral DNA was carried out on high molecular weight DNA prepared by the method Shih and Weinberg (1982) and fractionated on 0.8% agarose gels. The DNA was transferred to Zeta Bind (CUNO Labs, Meriden, Conn.) and hybridized by standard methods. Southern, 1975; Maniatis et al., *Molecular Cloning: A Laboratory Manual*, Cold Spring Harbor Laboratory, Cold Spring Harbor, N.Y. (1982). The serum free medium used was the N2 medium of Bottenstein and Sato (1979). The co-cultures were carried out after labelling the immortal cells with either fluorescein succinimidylester (Bronner-Fraser, M., *Journal of Cellular Biology*, 101:610 (1985)), the carbocyanine dye diI (Honig, M.G. and R.I. Hume, *Journal of Cellular Biology*, 103:171-187 (1986)) or rhodaminated latex beads (Katz et al., 1984). These labelled cells were then added to primary cultures of E14 cerebral cortex or P2 cerebellum one day after the primary cells were plated. The double label experiments with Rat 401 and rabbit anti-neurofilament antibody used the cross reaction between anti-MSH antibody and neuro-filament analyzed by Verhaagen et al. (1986).

v-myc and SV40 T antigen have previously been shown to be efficient in establishing rodent fibroblast cell lines. Land, H. et al., *Nature*, 304:596-602 (1983); Jat and Sharp, *Molecular and Cellular Biology*, 6:1204-1217 (1986). In contrast the neu oncogene has not previously been shown to establish primary rodent cell lines. However, activated neu is associated with neuroblastomas and glioblastomas (Schechter, A.L. et al., *Nature*, 312:513-516 (1984)) and the cellular neu is known to be expressed at the transcriptional and translational levels in the early nervous system. SV40 virus has been shown to generate cell lines with either neuronal or glial properties (DeVitry, F. et al., *Proceedings of the National Academy of Sciences, USA*, 77:4165-4169 (1974); Neto, V.M. et al., *Dev. Brain Res.*, 26:11-22 (1986)).

Figure 1:
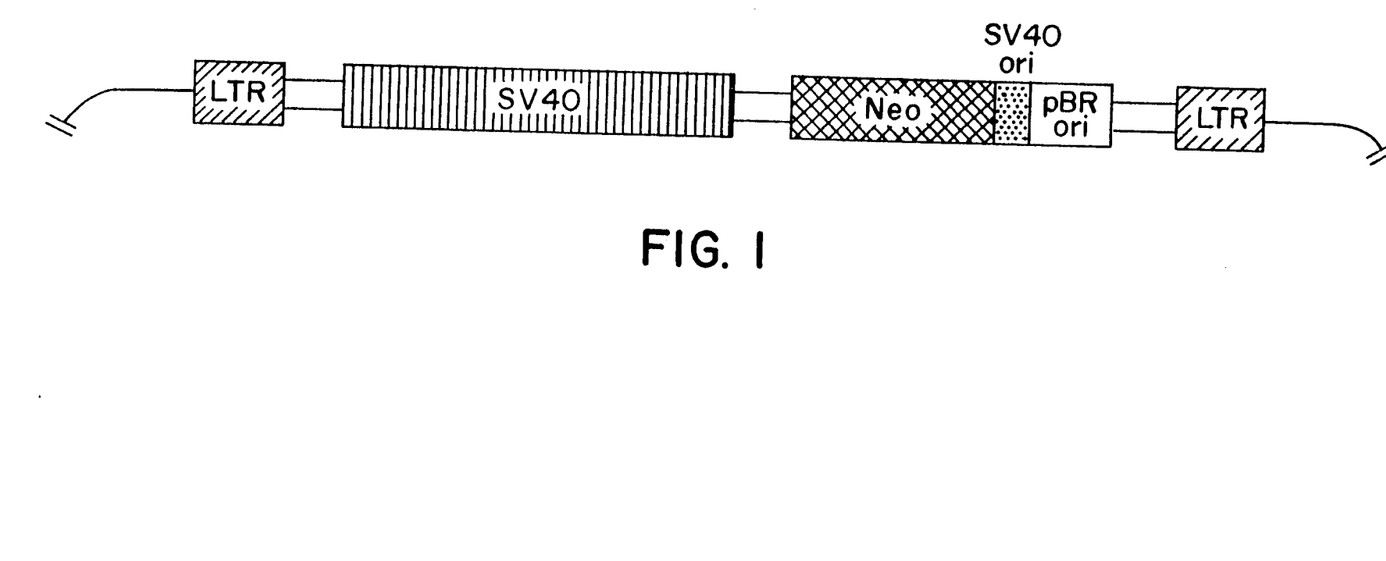
FIG. 1 is a schematic representation of the plasmid pZipSV40tsA58, in which the genomic BglI-Hpa I fragment (nucleotides 5235-2666) derived from the early region of the SV40 mutant tsA58 was inserted into the shuttle vector pZipNeoSV(X)1 (Cepko, C. et al., Cell, 1984) with Bam HI linkers.

Details of the construction of the v-myc transducing retrovirus can be found elsewhere (Dotto et al., 1986). The neu transducing retrovirus was a generous gift of Dr. C.I. Bargmann. SV40 T antigen has another advantage as it is available in a tight temperature sensitive form, which makes it possible to switch off the function of the oncogene by raising the temperature of cell growth. Tegtmeyer, P., *Journal of Virology*, 15:613-618 (1985); Tegtmeyer, P., In: J. Tooze (ed.), *Molecular Biology of Tumor Viruses* (2d ed.), Cold Spring Harbor Laboratory, pp. 297-338 (1980). A transducing retrovirus carrying the tsA58 mutant form of SV40 large T antigen was constructed (FIG. 1 and Example 1). This feature makes it possible to determine whether precursor cell lines would differentiate simply by growing the cells at an elevated temperature where T antigen is rapidly degraded.

The three recombinant retroviruses were all constructed by inserting DNA sequences encoding the oncogenes into the unique BamHI site of the pZip-NeoSV(X)1 vector (FIG. 1); the genes were inserted in the sense orientation with respect to retroviral transcription driven by the cis-acting transcriptional regulatory sequences in the left-hand long terminal repeat (LTR). Previous work has shown that different regulatory sequences allow the same oncogene to interact with different cell types. Because the only differences in the three retroviruses used here were in the coding sequences, any differences in the derived cell lines must be due to the oncogenes themselves and not to the regulatory sequences controlling transcription. All the pZip-NeoSVtsA58 producer cell lines were shown to synthesize virus which only transduce large T antigen. Thus the reported enhancement of transformation by SV40 small T antigen (Bikel et al., 1987) is not a complicating factor here.

Properties of Cerebellar Cell Lines

To be a candidate for immortalization, a cell type must be both present and proliferating in primary culture. The antigenic and proliferative status of P2 cerebellar cells in dissociated tissue culture was measured by immunohistochemistry and thymidine auto-radiography. Rat 401 positive cells are present in short term primary culture. The number of cells expressing GFAP is very low. The immunohistochemical data also shows that vimentin positive cells are present in primary culture. Antigenic and autoradiographic double label showed that Rat 401 positive and vimentin positive cells proliferate in primary culture but the GFAP positive cells are quiescent.

After infection and selection, isolated colonies were picked. Cell lines were characterized immunohistochemically with Rat 401, anti-GFAP and anti-vimentin antibodies. As shown in Table 3, all but one of the derived cell lines were Rat 401 positive and all were vimentin positive. GFAP expression was found in all of the cell lines derived from myc and neu infection; in contrast the SV40 immortalized cell lines were GFAP negative at the permissive temperature. These results show that it is possible to obtain cell lines expressing markers characteristic of three proliferating populations defined in Tables 2 and 3.

TABLE 1

Proportion of Rat 401 and GFAP positive P3 cerebellar cells double labelled with other antibodies.

| Rat 401 +, | 96% | vimentin + |

TABLE 1-continued

Proportion of Rat 401 and GFAP positive P3 cerebellar cells double labelled with other antibodies.

| Rat 401 +, | 53% | GFAP + |
| GFAP +, | 77% | Rat 401 + |
| GFAP +, | 80% | vimentin + |

TABLE 2

Proportion of antibody labelled cells which are also radiolabelled by an in vivo pulse of tritiated thymidine two hours before cell dissociation.

| Antibody | % cells radiolabelled on postnatal day | | | | |
|---|---|---|---|---|---|
| | 2 | 7 | 9 | 12 | 15 |
| Rat 401 | 8 | 8 | 9 | — | — |
| vimentin | 17 | 16 | 20 | 21 | 25 |
| GFAP | 9 | 11 | 10 | 6 | 5 |

TABLE 3

Antigenic profile of cerebellar cell lines.

| Immortalizing gene | No. of lines | Primary antibodies | | |
|---|---|---|---|---|
| | | Rat 401 | Vimentin | GFAP |
| SV40tsA58 | 9 | + | + | − |
| | 1 | − | + | − |
| v-myc | 31 | + | + | + |
| neu | 4 | + | + | + |

Two of the SV40 cell lines were grown at 33° C. and 39° C. and immunohistochemically analyzed for differentiation. The ST15I cell line was Rat 401 negative and did not differentiate at 39° C. in fetal calf serum. The ST15A line was used as a representative of the Rat 401 positive class. The results for ST15A show, as expected, that at the nonpermissive temperature, the cells lose T antigen expression. At the elevated temperature, these cells also lose Rat 401 antigenicity and gain GFAP expression. This antigenic switch in the cells is remarkably complete. At 33° C. Rat 401 negative cells or GFAP positive cells occur with a frequency of less than $10^{-3}$ at 33° C. After several days at 39° C., the majority (95%) of the ST15A cells were Rat 401 negative and GFAP positive. An increase in GFAP expression was confirmed by immunoblotting of total proteins extracted from cells grown at the permissive and nonpermissive temperature. Immunoblotting also showed that T antigen levels fall at the non-permissive temperature. The large cultures necessary for protein chemistry differed from the analytical cultures used for the immunohistochemical analysis as Rat 401 expression remained in 25% of the cells after 10 days of growth at the elevated temperature. Vimentin levels were unchanged.

ST15A were grown in the N2 medium of Bottenstein and Sata (1979). After 5 days at 39° C., cells with a neuronal morphology, which react with the antineurofilament monoclonal antibody SMI 31, were seen. After nine days in N2 medium, the proportion of SMI 31 positive cells increased (to 90% in some cultures) and cells with very long neurites (greater than 300 microns) were present. Cells with this highly distinctive neuronal morphology were present both at 33° C. and 39° C.

When live ST15A cells grown in 10% fetal calf serum were stained with an anti-galactocereberoside monoclonal antibody, approximately 1% of the cells were positive. The labelling of live cells and the distribution of the antigen shows that this is a surface component that is recognized by the anti-gal C antibody. The frequency of anti-GalC labelled cells was enhanced when ST15A cells were grown at the non-permissive temperatures. Galactocereberoside expression has been extensively used as a marker for commitment to oligodendrocyte differentiation (Raff, M.C. et al., *Nature*, 274:813-186 (1978), 1979; Schachner, M. and M. Willinger, In: *The Menarini Series of Immunopathology*, Vol. 2, pp. 37-60 (1979).

As the mechanisms controlling the differentiation of the neuroepithelium depend on cell interaction, differentiation of tsA cerebellar cell lines upon co-cultivation with primary embryonic brain cells was assessed. To identify the clonal immortal cells in the presence of primary cells, they were first labeled internally with either the succinimidyl ester of fluorescein (Bronner-Fraser, M., *Journal of Cellular Biology*, 101:610 (1985)) or the lipid soluble carbocyanine dye diI (Honig, M. G. and R. I. Hume, *Journal or Cellular Biology*, 103:171-187 (1986)). These internally labelled cells were then analyzed after they were added to primary rat cultures. The primary cells were derived from either the E14 cerebral cortex or from postnatal day 3 cerebellum. The mixed cultures were processed immunohistochemically with anti-T, anti-neurofilament, anti-vimentin, anti-GFAP, Rat 401 and the appropriate second antibody, tsA immortalized cells were identified by the internal label and the binding of antibody established in the same cell.

The initial experiments using this paradigm were carried out at 33° C. because the red nuclear T antigen fluroescence serves as a control for the internal labelling method. No internally labelled T antigen negative cells were seen. Confidence in these results is high because for each antibody there are large numbers of primary cells which are not internally labelled which acts as controls for the specificity of antibody staining.

In the presence of primary brain cells ST15A, cells can lose vimentin and Rat 401 antigenicity and gain either GFAP or neurofilament reactivity. Three different lines of evidence suggest that ST15I can differentiate into neurons: Firstly, many of the fluoroscein labelled cells adopt a morphology of small cell bodies with multiple processes. Secondly, like primary neurons these small ST15I cells are often found in clumps over flat non-neuronal cells. Thirdly, the processes of these small ST15I cells can be stained with an anti-neurofilament monoclonal antibody. ST15I cells which express the Rat 401 antigen were also found in co-culture In the Rat 401 positive ST15I cells shown, the antigen is restricted to a small perinuclear region. This distribution is also characteristically found in primary neuroepithelial cells as they differentiate from the Rat 401 positive precursor state to the neurofilament positive differentiated neuron.

Cells with neuronal properties were also produced when the v-myc induced cell line M15B was treated with dibutryl cyclic AMP and retinoic acid. This induction is not complete, but characteristically occurs in a colonial manner, suggesting that a commitment step occurs in a proliferating cell which subsequently differentiates into neurons or that local interactions are important in neuronal induction.

Southern blot analysis was used to determine whether the cell lines were clonal, panel A was hybridized with SV40 probe and panel B with neomycin probe. The SV40 sequences were released from flanking DNA by Bam HI digestion yielding a 2.3 Kb fragment designated b. The size of this fragment is too small to encode the small t antigen transcript and confirms the immunohistochemistry and immunoblotting data, showing that the pZipSVtsA58 retrovirus transduces large T antigen. Xba cuts in the viral LTR sequences releasing a single full length proviral sequence from ST15A and ST15I. EcoRI and Bgl II digestion cuts once in the provirus, yielding only a single fragment in ST15A and ST15I containing SV40 sequences and flanking cellular DNA. This data demonstrates that the ST15A and ST15I cells carried only a single insertion. In contrast, the M15b cells showed two large neomycin complementary bands. These two bands are found in the same ratios in multiple subclones of M15B suggesting that the M15B cell line as two independent viral insertion sites and is also a clonal cell line.

The present data suggests that the use of the tsA58 variant of SV40 T antigen favors the differentiation of the multipotential brain precursor cell at the non-permissive temperature of 39° C. The core body temperature of the rat is 39° C., suggesting that ts cell lines may differentiate when transplanted into the developing CNS. Wild type T immortalized cells have been transplanted into the immediately postnatal CNS of the rat. Results showed that as many as one million cells can be placed in the CNS, where they remain for several months without any gross indication of tumor formation (McKay et al., 1987). Transplantation of conditionally immortalized cell lines into the developing nervous system offers the most rigorous assay for the differentiation potential of these cell lines. Transplantation of primary neuroepithelium into the lesioned adult CNS has been used to restore behavioral function to lesioned animals. It may be possible to use cell lines in place of primary cells allowing a detailed analysis of the molecular genetics of behavioral recovery.

EXAMPLE 3

Infection of Optic Nerve Primary Cultures With Retrovirus ts U19

Optic nerve from 4-6 rats (P4) were dissociated according to the following protocol:
  i) The nerves were placed in 2 ml of Basal Eagles Medium (BEM) with 0.02M Hepes (Sigma, T5391) and collagenase 0.02% (Sigma, type IV, C5138) for 15 minutes at 37° C.
  ii) The BEM was then removed and 2 ml of HBSS, $Cs^{++}$ and $Mg^{++}$ "free" and 0.25% trypsin were added for 15 minutes at 37° C. (40X, Sigma T0511)
  iii) Cells were checked to determine whether they had begun to dissociate. Step i) and ii) were repeated, as required.
  iv) 1 ml of media was removed and 1 ml of Dulbecco's Modified Eagles Medium (DMEM).10% FCS was added. The nerves were panned up and down 3-5X through an 18 gauge needle with a 2 ml syringe. This was repeated three times through a 21 gauge needle.
  v) Large pieces of nerve were removed and the cell suspension was centrifuged to remove the digestion enzyme.
  vi) The pellet was resuspended in DMEM with 10% fetal calf serum (FCS) and were plated on polyornithine-covered dishes.

2. One or two days after dissociation, the medium was replaced with psi 2 supernatant (producer cells). ml of medium ($10^4 - - 10^5$ cfu/ml.) were added to each 2.5 cm dish. Polybrene (Sigma, P4S15) was also added to each dish, to a final concentration of 8 ug/ml. Cells were incubated at 33° C. for 2-3 hrs.

3. The virus-containing medium was removed and replaced with 2.5 ml of BMEM/10% FCS (same as in Step 1 vi).

4. Two days later, the infected cells were split 1:2 to 1:5. At this time G418 (Geneticin, Sigma G9516) was added to 200 micrograms/ml).

5. The medium was changed every 4.5 days and G418 was kept at the same concentration. Colonies began to form between 2-3 weeks later.

Cloning Cell Lines 1. 24 well petri dishes were treated with pOrn.
2. Cloning rings (glass, 7 mm θ and about 7 mm height) were placed with high vacuum gresse (Down Corning from Dupont) on a colony and 30-100 lambda of 1X trypsin/EDTA was added. Detachment of cells was checked under a microscope and cells were dissociated with 200 lambda pipetor and transferred to 24 wells/dish.
3. The clones were then assayed for the markers described previously.

Construction of Plasmid (pZip tsa 58 U19 or pts U19)

Figure 2A:
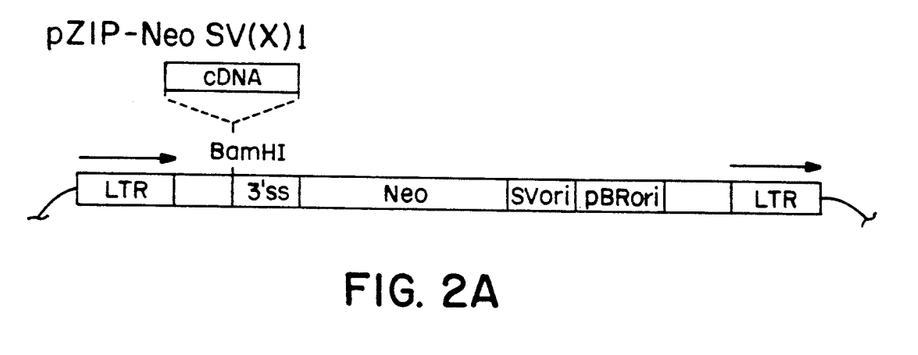
FIG. 2A is a schematic representation of plasmid pZipNeoSV(X)1 (Cepko, C. et al., Cell, 1984).
Figure 2B:
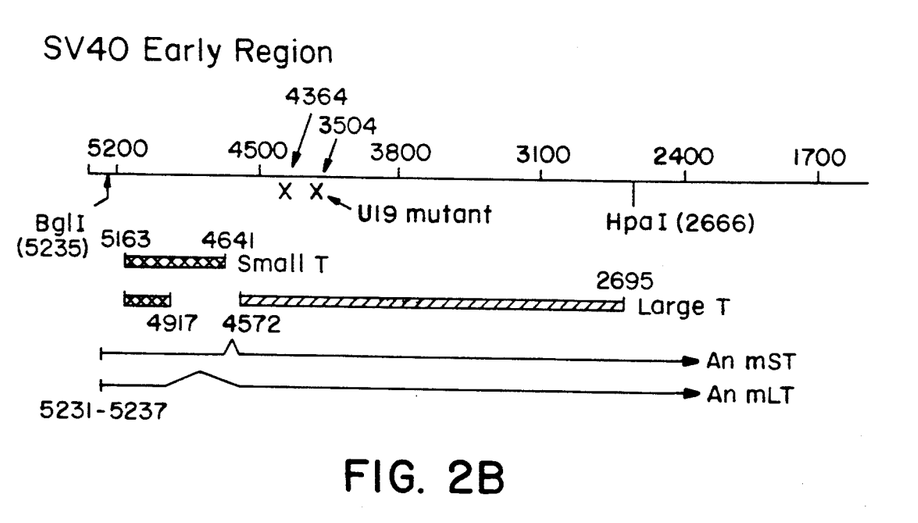
FIG. 2B is a schematic representation of the hybrid of the SV40 T antigen gene, U19, which was constructed using the pZiptsA58 and the U19 mutant.

The plasmid pZiptsa58U19 or ptsU19 is represented in FIG. 2. U19 is a variant of SV40 T antigen, described by Paucha and co-workers. Paucha, E. et al., *Journal of Virology*, 57:50-64 (1986). The U19 and tsA58 mutations occur in different parts of the large T antigen; Paucha et al. describe mutation of the large T antigen sequence from serine (amino acid position 152) and arginine (amino acid position 154) to, respectively, asparagine and lysine in the U19 mutant.

1. The tsA58 temperature sensitive form of the SV40 T antigen was placed in the pZipNeo SV (X)1 vector by inserting the whole early region (BglI-HpaI) of tsA58 into the Bam Hl site.
2. The hybrid of the SV40 T antigen gene, tsU19, was constructed using the pZip tsA58 and the U19 mutant.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method of immortalizing mammalian neural cells, to produce immortalized cells which are capable of multipotential differentiation, comprising the steps of:
   a) growing embryonic mammalian neural precursor cells in primary culture under permissive conditions;
   b) selecting embryonic mammalian neural precursor cells which are capable of multipotential differentiation with an antibody which recognizes a marker protein expressed by neural precursor cells which is recognized by Rat 401 antibody;
   d) introducing into appropriately-selected mammalian neural precursor cells a growth-promoting gene which is the temperature sensitive domain of the tsA58 strain of the Sv40 virus and is activated under said permissive conditions, said growth-promoting gene conferring on said neural precursor cells the ability to grow in tissue culture, to produce immortalized cells containing said growth-promoting gene which are capable of multipotential differentiation; and
   d) selecting neural cells containing said growth-promoting gene which are capable of multipotential differentiation and maintaining them under permissive conditions and in medium appropriate for cell growth, for sufficient time for cell growth.

2. Immortalized embryonic mammalian cells containing a growth promoting gene which is the temperature-sensitive domain of the tsA58 strain of the SV40 virus and capable of multipotential differentiation produced by the method of claim 1.

3. A method of producing, differentiated mammalian neural cells, comprising;
   a) introducing into embryonic mammalian neural precursor cells, which have been selectively isolated with an antibody which recognizes a marker protein expressed by neural precursor cells which is recognized by Rat 401 antibody and are capable of multipotential differentiation, a retroviral vector comprising a growth-promoting gene which is the temperature-sensitive domain of the tsA58 strain of the SV40 virus;
   b) culturing cells produced in (a) at a temperature of approximately 33° C. and under conditions sufficient for cell growth;
   c) shifting the temperature of the cultured cells to approximately 39° C.; and
   d) maintaining the cells under conditions appropriate for and for sufficient time for cell differentiation to occur.

4. Differentiated mammalian neural cells, containing a growth-promoting gene which is the temperature-sensitive domain of the tsA58 strain of the SV40 virus, produced by the method of claim 3.

5. Differentiated cells of claim 4 selected from the group consisting of neuronal cells and glial cells.

6. An immortalized cell line, capable of multipotential differentiation produced by incorporating into embryonic mammalian nervous system cells, which have been selectively isolated with an antibody which recognizes a marker protein expressed by neural precursor cells which are recognized by Rat 401 antibody and are capable of multipotential differentiation, a retroviral vector comprising a growth-promoting gene which is the temperature-sensitive domain of the tsA58 strain of the Sv40 virus and a gene encoding drug resistance, culturing said cells at a temperature of approximately 33° C. under conditions sufficient for and for sufficient time for cell growth to occur.

7. The method of immortalizing mammalian neural cells of claim 1 wherein in step b, the embryonic mammalian neural precursor cells are selected by Rat 401 antibody.

8. The method of producing differentiated mammalian neural cells of claim 3, wherein in step a the embryonic mammalian neural precursor cells are selectively isolated using Rat 401 antibody.

9. The immortalized cell line of claim 6 wherein the embryonic mammalian nervous system cells are selectively isolated by Rat 401 antibody.

10. The oligodendrocyte optic nerve cell line, ts U195, containing a growth-promoting gene which is the temperature sensitive domain of the tsA58 stain of the SV40 virus, deposited at the American Type Culture Collection under accession number CRL 9729.

* * * * *